United States Patent
Xie

(10) Patent No.: US 11,906,816 B2
(45) Date of Patent: Feb. 20, 2024

(54) GOGGLES AND AIR FILTER COMBINATION

(71) Applicant: SHENZHEN AURORA TECHNOLOGY LIMITED, Shenzhen (CN)

(72) Inventor: Qingbo Xie, Guangdong (CN)

(73) Assignee: SHENZHEN AURORA TECHNOLOGY LIMITED, Shenzhen (CN)

(*) Notice: Subject to any disclaimer, the term of this patent is extended or adjusted under 35 U.S.C. 154(b) by 786 days.

(21) Appl. No.: 16/932,865

(22) Filed: Jul. 20, 2020

(65) Prior Publication Data
US 2020/0348539 A1 Nov. 5, 2020

(30) Foreign Application Priority Data
Jun. 15, 2020 (CN) .......................... 202021098393.1

(51) Int. Cl.
*G02C 11/08* (2006.01)
(52) U.S. Cl.
CPC .................................... *G02C 11/08* (2013.01)
(58) Field of Classification Search
CPC .......... G02C 11/08; G02C 11/00; A61F 9/028
See application file for complete search history.

(56) References Cited

U.S. PATENT DOCUMENTS

| | | | | |
|---|---|---|---|---|
| 4,443,893 A | * | 4/1984 | Yamamoto ............. | G02C 11/08 2/436 |
| 5,452,480 A | * | 9/1995 | Ryden .................... | G02C 11/08 2/436 |
| 6,704,944 B2 | * | 3/2004 | Kawainshi ............. | A61F 9/028 2/436 |
| 7,802,318 B2 | * | 9/2010 | Chen ...................... | A42B 3/286 2/410 |
| 9,066,791 B2 | * | 6/2015 | Nolan .................... | A61F 9/028 |
| 9,839,166 B2 | * | 12/2017 | Kim .................. | G02B 27/0006 |
| 9,980,416 B2 | * | 5/2018 | Reynolds ........... | H05K 7/20972 |
| 10,379,583 B2 | * | 8/2019 | Allin ........................ | G06F 1/20 |
| 2011/0285957 A1 | * | 11/2011 | Mikulenka .............. | A61F 9/068 2/15 |
| 2016/0004085 A1 | * | 1/2016 | Stroetmann .......... | G02B 27/017 345/8 |
| 2016/0067367 A1 | * | 3/2016 | Jin .......................... | A61L 9/042 239/152 |
| 2016/0070120 A1 | * | 3/2016 | Cornelius ............... | A61F 9/029 219/211 |
| 2018/0239131 A1 | * | 8/2018 | Cornelius ............. | G06T 19/006 |

* cited by examiner

*Primary Examiner* — Bao-Thieu L Nguyen
(74) *Attorney, Agent, or Firm* — Westbridge IP LLC

(57) ABSTRACT

A goggles and air filter combination includes goggles including a container on a top, a frame, an eyeglass held by the frame, and a bridge; a strap having two ends releasably attached to two ends of the frame respectively; and an air filter including a housing disposed in the container, a centrifugal fan disposed in the housing, and a filter element disposed on a top of the centrifugal fan. The air filter communicates with the eyeglass.

4 Claims, 3 Drawing Sheets

GOGGLES AND AIR FILTER COMBINATION

BACKGROUND OF THE INVENTION

1. Field of the Invention

The invention relates to eye protection devices and more particularly to a goggles and air filter combination capable of removing moisture from the eyeglass when the air filter mounted on the goggles is activated.

2. Description of Related Art

Goggles are forms of protective eyewear that usually enclose or protect the area surrounding the eye in order to prevent particulates, water or chemicals from striking the eyes. They are used in chemistry laboratories, snow sports and swimming. However, conventional goggles are disadvantageous because fog may generate on the spectacles to blur view. Further, a user may feel a degree of discomfort because the goggles are tightly fitted on the face.

Thus, the need for improvement still exists.

SUMMARY OF THE INVENTION

The invention has been made in an effort to solve the problems of the conventional art including fog generated on the spectacles and discomfort by providing a goggles and air filter combination having novel and nonobvious characteristics.

To achieve above and other objects of the invention, the invention provides a goggles and air filter combination comprising goggles including a container on a top, a frame, an eyeglass held by the frame, and a bridge; an air filter including a housing disposed in the container, the air filter being configured to communicate with the eyeglass; and a strap; wherein the air filter further comprises a centrifugal fan disposed in the housing and a filter element disposed on a top of the centrifugal fan.

Preferably, the strap has two ends releasably attached to two ends of the frame respectively.

Preferably, the housing is releasably disposed in the container.

Preferably, the housing includes a first compartment and a second compartment with the centrifugal fan disposed therein, and wherein the air filter further comprises a power supply disposed in the first compartment.

Preferably, the air filter further comprises a printed circuit board (PCB) disposed on a top of the power supply and electrically connected to the centrifugal fan and the power supply respectively.

Preferably, the air filter further comprises a cover releasably disposed on the housing with the PCB directly disposed thereunder, an on/off switch disposed on a top of the cover.

Preferably, the housing further comprises an opening through a front surface, the opening being configured to communicate with the second compartment and the eyeglass respectively.

The invention has the following advantageous effects in comparison with the prior art: the centrifugal fan can draw external air through the filter element which removes solid particulates such as dust, pollen, mold, and bacteria from the air. Further, the centrifugal fan can move clean air from the filter element to the eyeglass so that the air can remove fog, moisture, etc. from the eyeglass. The eyeglass is curve flat and adapted to tightly fit on the face of the user, so that a user may feel a degree of comfort because the goggles are tightly fitted on the face. The housing is releasably disposed in the container by snapping so that it is easy to replace components of the air filter if such need arises.

The above and other objects, features and advantages of the invention will become apparent from the following detailed description taken with the accompanying drawings.

DETAILED DESCRIPTION OF THE INVENTION

Figure 1:
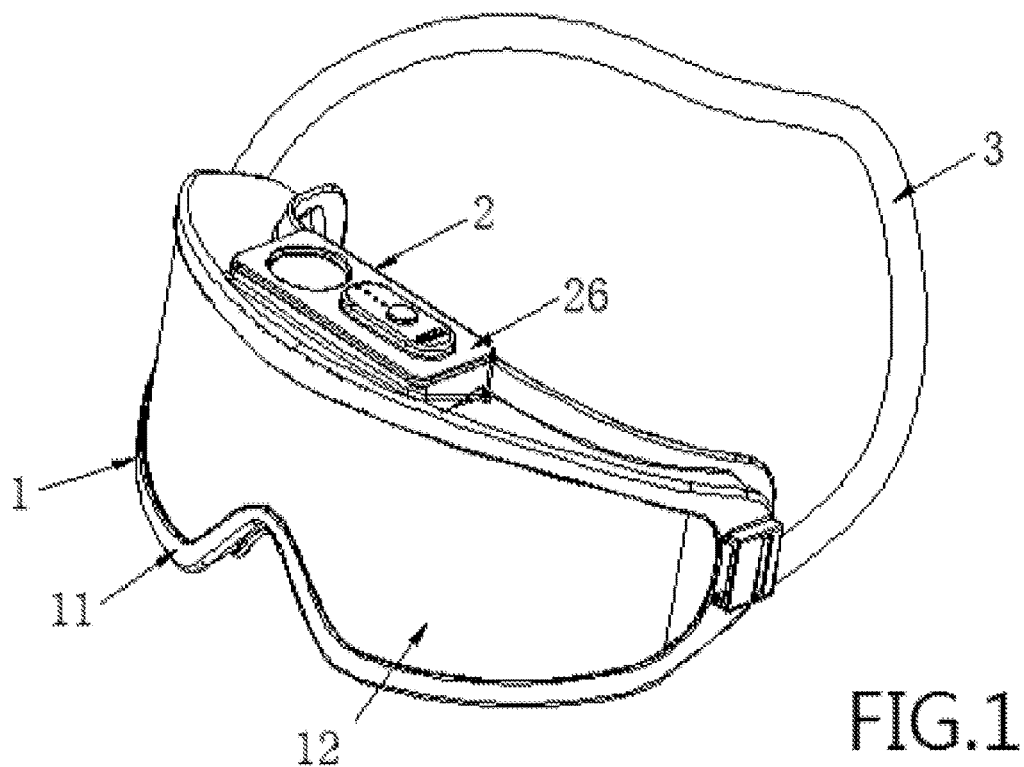
FIG. 1 is a perspective view of a goggles and air filter combination according to the invention.
Figure 2:
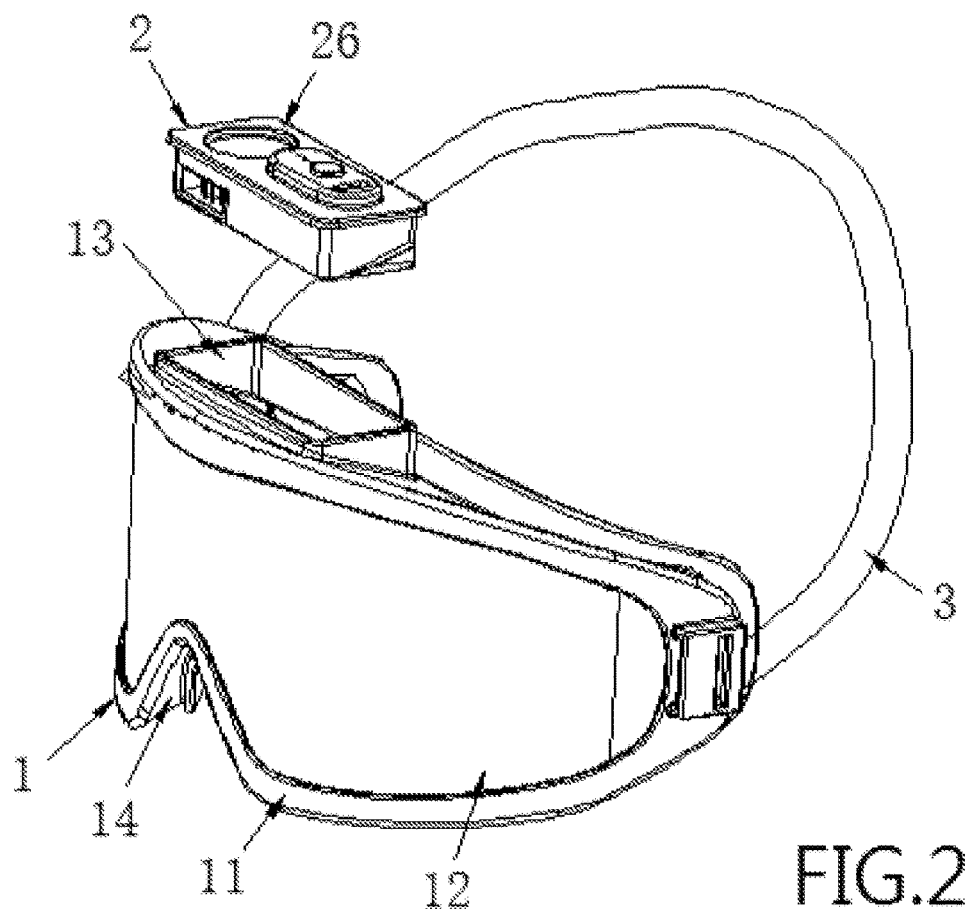
FIG. 2 is a perspective view of FIG. 1 with the air filter detached.
Figure 3:
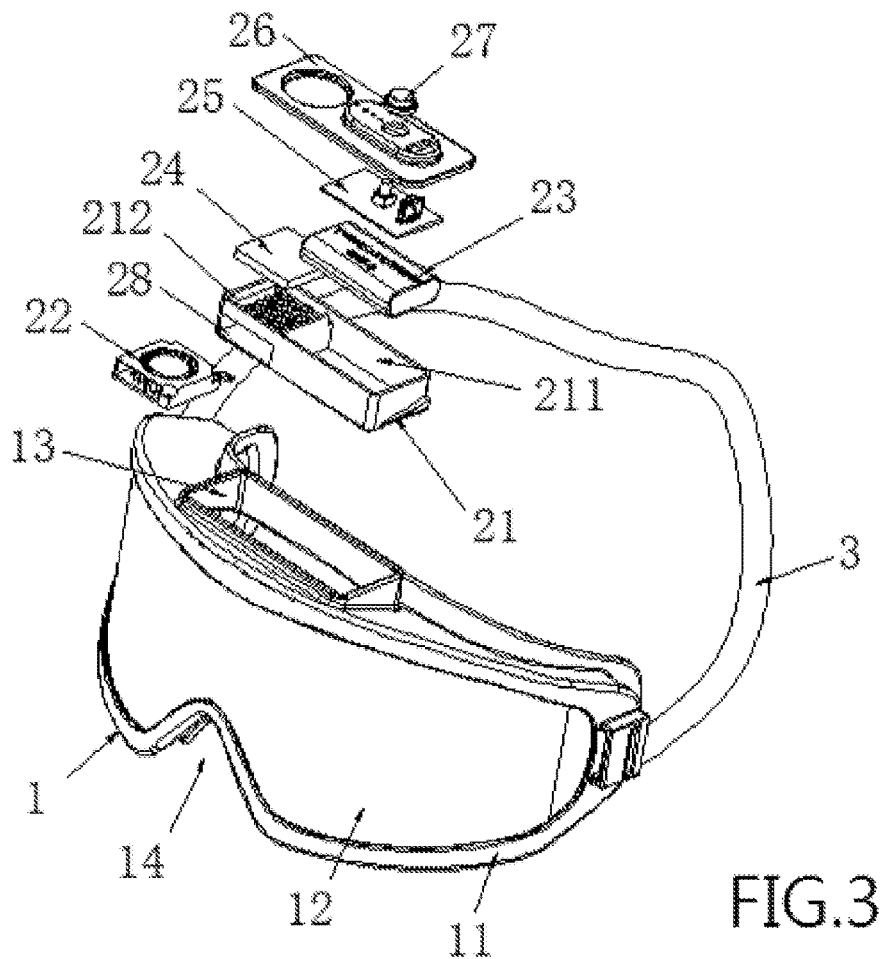
FIG. 3 is a perspective exploded view of FIG. 1 showing components of the air filter.
Figure 4:
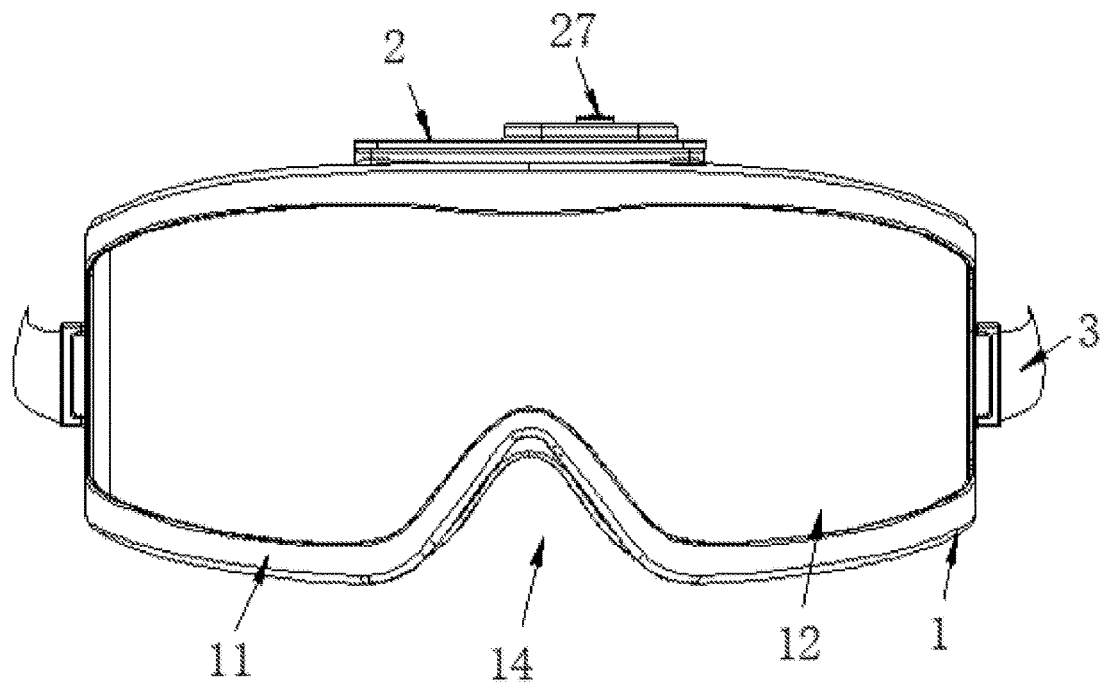
FIG. 4 is a front view of FIG. 1.
Figure 5:
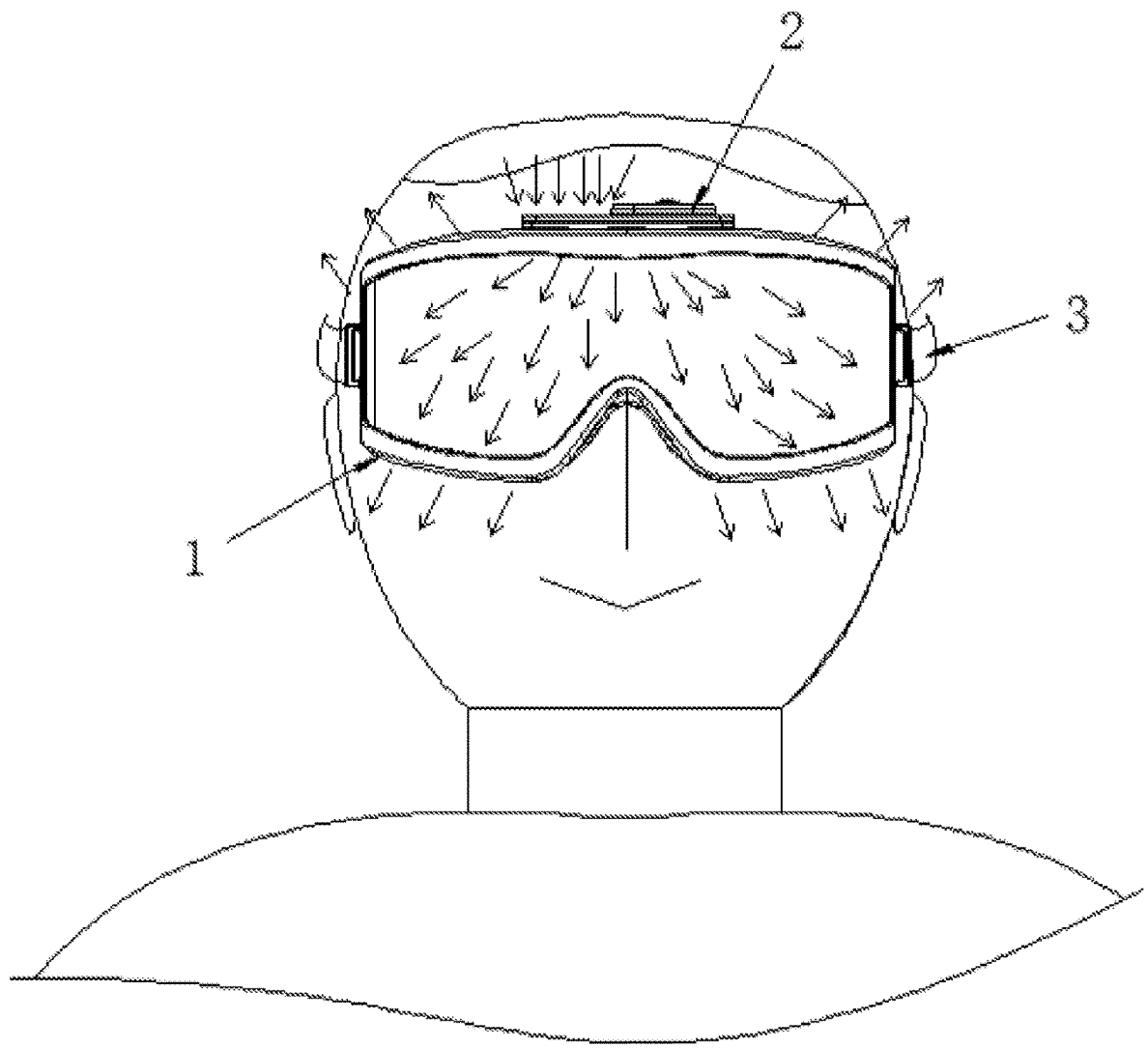
FIG. 5 schematically depicts the goggles and air filter combination worm by a user and air flow through the eyeglass.

Referring to FIGS. 1 to 5, a goggles and air filter combination in accordance with the invention comprises goggles 1, an air filter 2 and a strap 3 as discussed in detail below.

The air filter 2 is mounted a top of the goggles 1. The goggles 1 include a frame 11, an eyeglass 12 held by the frame 11, a container 13 on a top, and a bridge 14 configured to rest on the nose of a user. The eyeglass 12 is curve as shown (or flat) to tightly fit on the face of the user, so that a user may feel a degree of comfort because the goggles are tightly fitted on the face. The bridge 14 is made as small as possible so as to increase the user's field of view. The air filter 2 includes a housing 21 releasably disposed in the container 13 by snapping so that it is easy to replace components of the air filter 2 if such need arises. The air filter 2 further comprises a centrifugal fan 22 and a filter element 24 on a top of the centrifugal fan 22. The centrifugal fan 22 can draw external air through the filter element 24 which removes solid particulates such as dust, pollen, mold, and bacteria from the air. Further, the centrifugal fan 22 can move clean air from the filter element 24 to the eyeglass 12 so that the air can remove fog, moisture, etc. from the eyeglass 12. The housing 21 includes a first compartment 211 and a second compartment 212 with the centrifugal fan 22 disposed therein. The air filter 2 further comprises a power supply (e.g., rechargeable battery) 23 in the first compartment 211, and a printed circuit board (PCB) 25 disposed on a top of the power supply 23 and electrically connected to the centrifugal fan 22 and the power supply 23 respectively. The power supply 23 is configured to supply electricity to the centrifugal fan 22. A power socket (not shown), a push-button (not shown) and a power-on light (not shown) are provided the PCB 25. Detailed description of the centrifugal fan 22, the power supply 23, the PCB 25, the power socket, the push-button and the power-on light are omitted herein because they are known in the art.

The air filter 2 further comprises a cover 26 releasably mounted on the housing 21 with the PCB 25 directly disposed thereunder, an on/off switch 27 provided on a top of the cover 26, and an opening 28 through a front surface of the housing 21 to communicate with the second compartment 212 and the eyeglass 12 respectively.

The strap 3 has two ends attached to two clasps (not numbered) at two ends of the frame 11 respectively. Length of the strap 3 is adjustable and the clasps are known in the art.

While the invention has been described in terms of preferred embodiments, those skilled in the art will recognize that the invention can be practiced with modifications within the spirit and scope of the appended claims.

What is claimed is:

1. A goggles and air filter combination comprising:
   goggles including a frame, a container provided on the frame and over a nose of a user when worn and corresponding to a bridge of the frame, and an eyeglass held by the frame;
   an air filter including a housing disposed in the container, the air filter being configured to communicate with the eyeglass; and
   a strap;
   wherein the air filter further comprises a centrifugal fan disposed in the housing and a filter element disposed on a top of the centrifugal fan, the housing includes a first compartment and a second compartment with the centrifugal fan disposed therein, and wherein the air filter further comprises a power supply disposed in the first compartment.

2. The goggles and air filter combination of claim 1, wherein the air filter further comprises a printed circuit board (PCB) disposed on a top of the power supply and electrically connected to the centrifugal fan and the power supply respectively.

3. The goggles and air filter combination of claim 2, wherein the air filter further comprises a cover releasably disposed on the housing with the PCB directly disposed thereunder, an on/off switch disposed on a top of the cover.

4. The goggles and air filter combination of claim 1, wherein the housing further comprises an opening through a front surface, the opening being configured to communicate with the second compartment and the eyeglass respectively.

* * * * *